US007727517B2

(12) United States Patent
Pankiw et al.

(10) Patent No.: US 7,727,517 B2
(45) Date of Patent: Jun. 1, 2010

(54) STABILIZED BROOD PHEROMONE FOR MANIPULATING THE BEHAVIOR AND PHYSIOLOGY OF HONEY BEES (75) Inventors: Tanya Pankiw, College Station, TX (US); Jean Pierre Lafontaine, Ladner (CA); Norman Avelino, Richmond (CA)

(73) Assignee: Contech Enterprises Inc., Victoria, BC (CA)

( * ) Notice: Subject to any disclaimer, the term of this patent is extended or adjusted under 35 U.S.C. 154(b) by 745 days.

(21) Appl. No.: 11/470,762

(22) Filed: Sep. 7, 2006

(65) Prior Publication Data

US 2008/0124300 A1    May 29, 2008

(51) Int. Cl.
  *A01N 25/00* (2006.01)
  *A01N 37/00* (2006.01)
  *A61K 31/20* (2006.01)
  *A61K 31/201* (2006.01)
  *A61K 31/202* (2006.01)
  *A01K 51/00* (2006.01)
  *A31K 35/355* (2006.01)

(52) U.S. Cl. .................. 424/84; 514/546; 514/552; 514/558; 514/574; 514/734; 449/1

(58) Field of Classification Search ............... 514/546, 514/552, 558, 574, 734; 424/84; 449/1
See application file for complete search history.

(56) References Cited

U.S. PATENT DOCUMENTS

| 6,595,828 | B2 | 7/2003 | Page, Jr. et al. |
| 2002/0182977 | A1 | 12/2002 | Page, Jr. |
| 2006/0134178 | A1 | 6/2006 | Doisaki et al. |

OTHER PUBLICATIONS

Yoshida, H., Antioxidant Effects of d-Tocopherols at Different Concentrations in Oils During Microwave Heating, Oct. 1993, JAOCS, vol. 70, No. 10, pp. 989-995.*
tert-Butylhydroquinone, Product Sheet [online]. Chemical Land 21, Mar. 18, 2006, [retrieved on Mar. 12, 2009]. Retrieved from the Internet: <URL:http://web.archive.org/web/20060318051721/http://www.chemicalland21.com/specialtychem/finechem/TBHQ.htm>.*
Butylated Hydroxyanisole (BHA), Report on Carginogens Eleventh Edition [online], Apr. 24, 2006, [retrieved on Mar. 12, 2009]. Retrieved from the Internet: <URL: http://web.archive.org/web/20060424090541/http://ntp.niehs.nih.gov/ntp/roc/eleventh/profiles/s027bha.pdf>, p. 1-2.*
Ramalho & Neuza: "Antioxidantes utilizados em oleos, gorduras e alimentos gordurosos", Quimica Nova (Jul. 2006), 29(4): 755-760.
Halliwell et al.: "Free radicals and antioxidants in food and in vivo: what they do and how they work", Critical Reviews in Food Science and Nutrition (1995) 35(1&2): 7-20.
Anderson, C.A. et al., 2001. Teams in animal societies. Behav. Ecol. 12:534-540.

Al-Tikrity, W.S., et al. 1972. The relationship between the amount of unsealed brood in honeybee colonies and their pollen collection. J. Apic. Res. 11: 9-12.
Barker, R.J. 1971. The influence of food inside the hive on pollen collection. J. Apic. Res. 10: 23-26.
Crailsheim, K., et al. 1992. Pollen consumption and utilization in worker honeybees (Apis mellifera carnica): dependence on individual age and function. J. Insect Physiol. 38: 409-419.
Filmer, R.S. 1932. Brood area and colony size as factors in activity of pollination units. J. Econ. Entomol. 25: 336-343.
Free, J.B. 1967. Factors determining the collection of pollen by honeybee foragers. Anim. Behav. 15: 134-144.
Free, J.B. 1979. Managing honeybee colonies to enhance the pollen-gathering stimulus from brood pheromones. Appl. Anim. Ethol. 5: 173-178.
Herbert, E.W. 1992. Honey bee nutrition. pp. 197-233. In: Graham, J.M. (ed.). The hive and the honey bee. Rev. Ed. Dadant & Sons, Hamilton, Illinois.
Jaycox, E.R. 1970. Honey bee queen pheromones and worker foraging behavior. Ann. Entomol. Soc. Am. 63: 222-228.
Leconte, Y., et al. 1990. Identification of a brood pheromone in honeybees. Naturwissenschaften 81: 462-465.
Leconte, Y., et al. 2000. Primer effects of a brood pheromone on honeybee behavioural development. Proc. R. Soc. London B 268: 163-168.
Lindauer, M. 1952. Ein Beitrag zur Frage der Arbeitsteilung im Bienenstaat. Z. Vergl. Physiol. 34: 299-345.
Page, R.E., Jr., et al. 1998. The effect of genotype on response thresholds to sucrose and foraging behavior of honey bees (Apis mellifera L.). J. Comp. Physiol. A 182: 489-500.
Pankiw, T. 2003. Directional change in a suite of foraging behaviors in tropical and temperate evolved honey bees (Apis mellifera L.). Behav. Ecol. Sociobiol. 54: 458-464.
Pankiw, T. 2004a. Cued in: honey bee pheromones as information flow and collective decision making. Apidologie 35: 217-226.
Pankiw, T. 2004b. Brood pheromone regulates foraging activity of honey bees (Hymenoptera: Apidae). J. Econ. Entomol. 97: 748-751.
Pankiw, T. and R.E. Page, Jr. 1999. The effects of genotype, age, sex, and caste on response thresholds to sucrose and foraging behavior of honey bees (Apis mellifera L.). J. Comp. Physiol. A 185: 207-213.
Pankiw, T. and R.E. Page, Jr. 2000. Response thresholds to sucrose predict foraging division of labor in honey bees. Behav. Ecol. Sociobiol. 47: 265-267.

(Continued)

*Primary Examiner*—Johann R Richter
*Assistant Examiner*—Andriae M Holt
(74) *Attorney, Agent, or Firm*—Oyen Wiggs Green & Mutala LLP (57) ABSTRACT This invention relates to a stabilized honey bee pheromone and methods of stabilizing the honey bee brood pheromone, thereby enabling the production and sustained use of commercial products based on that pheromone. The stabilized pheromone can be used to manipulate the behavior and improve the performance of worker honey bees, resulting in overall increased vigor of the hive. The pheromone composition comprises two or more of ethyl linoleate, ethyl linolenate, ethyl oleate, ethyl palmitate, ethyl stearate, methyl linoleate, methyl linolenate, methyl oleate, methyl palmitate and methyl stearate and an antioxidant.

1 Claim, 4 Drawing Sheets

OTHER PUBLICATIONS

Pankiw, T. and R.E. Page, Jr. 2001. Brood pheromone modulates sucrose response threshold in honeybees (*Apis mellifera* L.). Behav. Ecol. Sociobiol. 49: 206-213.

Pankiw, T., et a. 2003. Effect of pheromones, hormones and handling on sucrose response thresholds of honey bees (*Apis mellifera* L.). J. Comp. Physiol. A 188:675-684.

Pankiw, T. and W.L. Rubink. 2002. Pollen foraging response to brood pheromone by Aftricanized and European honey bees (*Apis mellifera*). Ann. Entomol. Soc. Am. 95: 761-767.

Pankiw, T., R.E. Page, Jr. and M.K. Fondrk. 1998. Brood pheromone stimulates pollen foraging in honey bees (*Apis mellifera*). Behav. Ecol. Sociobiol. 44: 193-198.

Pankiw, T., et al. 2004a. The communal crop: Modulation of sucrose response thresholds of pre-foraging honey bees with incoming nectar quality. Behav. Ecol. Sociobiol. 55: 286-292.

Pankiw, T., et al. 2004b. Pheromone-modulated behavioral suites influence colony growth in the honey bee (*Apis mellifera*). Naturwissenschaften 91: 575-578.

Robinson, G.E. 1992. Regulation of division of labor in insect societies. Ann. Rev. Entomol. 37: 637-665.

Seely, T.D. and S.A. Kolmes. 1991. Age polytheism for hive duties in honey bees—illusion or reality. Ethology 87: 284-297.

Todd, F.E. and C.B. Reed. 1970. Brood measurement as a valid index to the value of honey bees as pollinators. J. Econ. Entomol. 63: 148-149.

* cited by examiner

STABILIZED BROOD PHEROMONE FOR MANIPULATING THE BEHAVIOR AND PHYSIOLOGY OF HONEY BEES

FIELD OF THE INVENTION

This invention relates to a stabilized honey bee pheromone and methods of stabilizing the honey bee brood pheromone, thereby enabling the production and sustained use of commercial products based on that pheromone. The stabilized pheromone can be used to manipulate the behavior and improve the performance of worker honey bees, resulting in overall increased vigor of the hive. Specific behaviors influenced by the stabilized pheromone applied on an inert substrate include: age of first foraging, proportion of workers that are foragers, ration of pollen to nectar foragers, pollen loading by individual bees, efficiency of pollination of target crops, consumption of supplementary diet components and antibodies, rearing of workers, and propensity to swarm. The stabilized pheromone can also be used to influence the development of the hypopharyngeal food gland and the production of protein by the gland. The stabilized foraging pheromone can further be used in conjunction with the honey bee queen mandibular gland pheromone, particularly in influencing pollination of target crop plants.

BACKGROUND OF THE INVENTION

A colony of honey bees, *Apis mellifera*, consists of a single queen, who is usually the mother of all other colony members, 10,000-30,000 semi-sterile female workers, and from zero to a few thousand males (drones), depending on the time of year. Eggs, larvae, and pupae are collectively referred to as brood. Female adult workers perform all of the behavioral tasks associated with colony growth and maintenance. Worker honey bees perform different tasks as they age, a phenomenon referred to as division of labor or temporal polyethism (Robinson 1992; Anderson and Franks 2001). When worker honey bees emerge from their cells as adults their first "job" is normally to clean cells. As the workers age they take on a succession of other jobs: feeding larvae, processing and storing food, secreting wax and constructing comb, and guarding the entrance to the hive. The most obvious change in behavior occurs when worker bees are about three weeks old, and they begin foraging (Lindauer 1952; Seeley and Kolmes 1991). Foraging labor is also divided, whereby some workers return to the colony carrying only nectar, some carry only pollen, and some return carrying both nectar and pollen. Pollen and nectar are sources of protein and carbohydrate, respectively.

Honey bee foragers collect pollen from available plant sources. They then return to the nest and deposit their loads of pollen directly into cells. Stored pollen is consumed by young nurse bees that use the proteins derived from the pollen to produce proteinaceous hypopharyngeal gland secretions that are fed to developing larvae (Crailsheim et al. 1992). By consuming pollen in this manner, nurse bees reduce the quantities of stored pollen. The presence of young larvae affects the proportion of foragers collecting pollen. The more larvae in a colony, the more pollen is collected by foraging workers (Al-Tikrity et al. 1972; Barker 1971; Free 1967, 1979; Jaycox 1970; Todd and Reed 1970).

The hypothesis that larval honey bees produce a pheromone that stimulates foraging (Filmer 1932: Free 1967) was tested and verified by Pankiw et al. (1998), who found a 2.5 fold increase in the number of pollen foragers when colonies with 1,000 larvae were provided with hexane extracts of 2,000 honey bee larvae. Pankiw et al. (1998) also found that the same hexane larval extract stimulated pollen foraging in colonies with no larvae, i.e. the extract replaced the larvae as a source of pheromone. Thus, bees apparently determine the number of larvae in a colony by sensing the concentration of chemicals in brood pheromone produced by the larvae.

Pankiw and Page (2001) and Page and Pankiw (2002) tested a synthetic pheromone blend that comprised ten esters of fatty acids (LeConte et al. 1990) in the following percentages: ethyl linoleate 1%, ethyl linolenate 13%, ethyl oleate 8%, ethyl palmitate 3%, ethyl stearate 7%, methyl linoleate 2%, methyl linolenate 21%, methyl oleate 25%, methyl palmitate 3% and methyl stearate 17%. This blend was found to lower the neurosensory response threshold to sucrose in worker bees, which is a measure of propensity to forage for pollen. Worker honey bees with low sucrose response thresholds are most likely to forage for pollen, and those with high response thresholds are most likely to forage for nectar (Pankiw and Page 2000; Pankiw 2003; Pankiw et al. 2004a). Within one hour of being placed in the center of a colony, larval extract or the synthetic brood pheromone blend increased the ratio of pollen to non-pollen foragers of colonies in an almond orchard. Based on their results, Pankiw and Page (2001) suggest that "brood pheromone modulates response threshold in pre-foragers, primes them to be pollen foragers, and releases pollen foraging behavior."

In a subsequent study, Pankiw et al. (2004b) exposed honey bee colonies to 2,000 larval equivalents (1.12 mg) of synthetic brood pheromone daily for 28 days. As well as increasing the number of pollen foragers, as predicted by earlier studies, brood pheromone had several other important effects. Compared to untreated control colonies, the weights of pollen loads returned to the hive were significantly greater in colonies treated with brood pheromone. Pheromone-treated colonies reared significantly more brood, as measured by the area of comb housing eggs, larvae and pupae. The number of adult honey bees that emerged from this brood was significantly greater in colonies treated with brood pheromone than in untreated control colonies. Thus the overall size of colonies was increased.

Brood pheromone can have dose-dependent effects (Pankiw 2004a; LeConte et al. 2000). At a low, biologically realistic dose of 2,000 larval equivalents, brood pheromone recruited honey bee workers to become foragers at an earlier age than in control colonies (Pankiw et al. 2004), whereas at a much higher dose of 6,200 larval equivalents, brood pheromone delayed the recruitment of workers to become foragers (LeConte et al. 2000).

Pankiw et al. (2004) found that although exposure to brood pheromone generally lowered the age of first foraging, the onset of foraging was delayed in a specialized cohort of worker bees that had a very high content of protein in their hypopharyngeal glands. This high protein level is an indication of increased probability of brood rearing behavior and a correspondingly higher quality of protein fed to larvae compared to that in control colonies.

Pankiw (2004b) found that the ratio of pollen foragers to non-pollen foragers increased within one hour of placement of 2,000 larval equivalents of synthetic brood pheromone into a honey bee colony. Foragers from pheromone-treated colonies returned with heavier pollen loads than foragers from control colonies, and this pollen was 43% more likely to originate from the target crop within which colonies were placed to ensure pollination. Non-pollen foragers, that may visit and pollinate more flowers than pollen foragers while searching for the best nectar sources, had more pollen grains on their bodies than non-pollen foragers from untreated control colonies. Similar to pollen foragers, these non-pollen foragers bore pollen that was 54% more likely to originate from the target crop than pollen borne by non-pollen foragers from control colonies. By increasing the activity of both pollen foragers and non-pollen foragers, brood pheromone has the potential to greatly increase the effectiveness of colonies used in custom pollination of target crops.

Another potential use for brood pheromone is stimulating the consumption of dietary protein supplements. Beekeepers commonly provide a protein supplement in winter or early spring to promote colony growth (Herbert 1992). Often an antibiotic is blended with the protein supplement as a prophylactic against larval bacterial diseases. However, because larvae are absent or at their lowest levels in late winter and early spring, there is very little, if any, brood pheromone being produced within the colony that might stimulate the consumption of protein and antibiotic dietary supplements, as well as hypopharyngeal gland development and protein biosynthesis. Administration of synthetic brood pheromone within a colony could provide the necessary stimulus.

Although the 10-component synthetic brood pheromone mimics natural pheromone extracts with respect to function, it lacks the potency of the natural pheromone (Pankiw 2004). This deficiency suggests that one or more components of the natural pheromone blend are yet to be identified.

Despite the practical promise of brood pheromone (Pankiw 2004b), no commercial products have been developed that incorporate its ten components, apparently because of their instability at room temperature. In fact, Page and Pankiw (2002) teach that the "synthetic brood pheromone is easily oxidizable, and must be stored in low-oxygen conditions, preferably at −20° C., and most preferably at −70° C. if it will be stored for any long period of time." Even freezing may not stabilize the pheromone. For example, crude honey bee larval extract lost all pheromonal activity after only three months in a laboratory freezer (T. Pankiw, Texas A&M University, unpublished observation). Thus any commercial product that incorporated either the natural or synthetic pheromone would have almost no shelf life, and would potentially lose all potency during storage and shipping. Freezing would be prohibitively expensive, and would probably not prolong the shelf life for an acceptable duration. Recognizing the instability of the synthetic pheromone, researchers have invariably provided their experimental bees with fresh pheromone each day, usually on glass plates (Pankiw et al. 1998; Pankiw and Page 2001; Page and Pankiw 2002; Pankiw and Rubink 2002; Pankiw et al. 2004b). In commercial operational use, daily application of pheromone would be impractical and expensive, and would not eliminate the need to freeze the pheromone during storage.

SUMMARY OF THE INVENTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification is to be regarded in an illustrative, rather than a restrictive, sense.

The invention is directed to a method of stabilizing honey bee brood pheromone comprised of two or more long-chain carboxylic acids, for example, C16 to C20 length carboxylic acids or their methyl or ethyl esters, specifically two or more of ethyl linoleate, ethyl linolenate, ethyl oleate, ethyl palmitate, ethyl stearate, methyl lenoleate, methyl linolenate, methyl oleate, methyl palmitate and methyl stearate by incorporating an antioxidant into the pheromone.

The antioxidant can be a food-grade antioxidant. In particular, the food-grade antioxidant can be selected from among the group comprised of (but not limited to) butylated hydroxyanisole, butylated hydroxytolulene, tertiary-butyl hydroquinone, polypropylene glycol, citric acid and vitamin E and its derivatives (tocopherols) or any combination of two or more of said antioxidants.

In the method, the antioxidant acts by inhibiting the breakdown of methyl linoleate, methyl linolenate, ethyl linoleate, ethyl linolenate, methyl oleate and ethyl oleate.

In another aspect, the invention is directed to a composition comprised of two or more of ethyl linoleate, ethyl linolenate, ethyl oleate, ethyl palmitate, ethyl stearate, methyl linoleate, methyl linolenate, methyl oleate, methyl palmitate, methyl stearate and one or more food-grade antioxidants selected from among the group comprised of (but not limited to) butylated hydroxyanisole, butylated hydroxytolulene, tertiary-butyl hydroquinone, polypropylene glycol, citric acid and vitamin E and its derivatives (tocopherols) for administration to honey bees or honey bee colonies.

The proportions by weight of the components of the composition can be ethyl linoleate (0.1-50%), ethyl linolenate (1.3-50%), ethyl oleate (0.8-50%), ethyl palmitate (0.3-50%), ethyl stearate (0.7-50%), methyl linoleate (0.2-50%), methyl linolenate (0.2-50%), methyl oleate (0.3-50%), methyl palmitate (0.3-50%), methyl stearate (1.7-50%), and antioxidant (0.001-50%).

The composition as described can be administered to honey bees, honey bee colonies or pollination units in an inert substrate selected from among the group comprised of paraffin, vegetable wax, beeswax, silica, alumina, cellulose, modified cellulose (paper and paper products), dried plant tissue, wood, or a synthetic polymer.

The method and the composition can be used to increase the ratio of pollen to non-pollen foragers among worker honey bees, or used to lower or delay the age of first foraging by worker honey bees, or can be used to increase the total number of foraging worker honey bees, or can be used to increase the load weight of pollen returned to the colony of pollen-foraging worker honey bees, or used to increase the number of pollen grains carried by the bodies of non-pollen-foraging worker honey bees, or used to increase the pollination of the target crop near or within which honey bee colonies or pollination units are placed, or used to stimulate hypopharyngeal brood food gland development and gland protein production in honey bee workers, or used to stimulate the consumption of dietary protein or other diet components and antibiotic supplements by honey bees.

In the method, continual administration of the composition to a honey bee colony for a period of about two weeks or longer can be used to increase the number of bees reared within the colony, or used to inhibit absconding (swarming) of bees from the colony.

In the method, the composition can be administered to honey bees, honey bee colonies or pollination units in combination with synthetic honey bee queen mandibular gland pheromone administered to honey bees, honey bee colonies or pollination units or to flowering plants on which enhanced pollination is desired.

DRAWINGS

Exemplary embodiments are illustrated in referenced figures of the drawings. It is intended that the embodiments and figures disclosed herein are to be considered illustrative rather than restrictive.

DETAILED DESCRIPTION OF THE INVENTION

Honey bee foraging pheromone is easily oxidizable and unstable at room temperature, loses bioactivity rapidly, and must be held under low oxygen conditions and preferably frozen at very low temperatures, e.g. −70° C., if it to be stored for long durations. Under normal conditions, any product based on the pheromone has almost no shelf life, and is not be commercially viable. Thus, apart from use of the pheromone in research, there has been no commercial application of the pheromone.

We have discovered that the honey bee brood pheromone can be stabilized for a substantial period of time by incorporating an anti-oxidant, particularly a food-grade antioxidant, into the pheromone. Stabilized brood pheromone formulations can be delivered to the hive on an inert substrate. Used alone, or with the honey bee queen mandibular pheromone, the brood pheromone can improve the performance of worker honey bees and enhance the overall vigor of the hive.

In general terms, the invention is directed to a method of stabilizing the honey bee brood pheromone using one or more acceptable anti-oxidants, especially one or more food-grade antioxidant, including (but no limited to) butylated hydroxyanisole, butylated hydroxytolulene, tertiary-butyl hydroquinone, polypropylene glycol, citric acid and vitamin E and its derivatives. Formulations of the ten-component pheromone that include an antioxidant can be delivered in a sustained manner to a hive on an inert substrate.

By using the antioxidant stabilizer tertiary-butylhydroquinone, we have discovered that certain unstable pheromone components, particularly methyl linoleate, methyl linolenate, ethyl linoleate and ethyl linolenate, but also including methyl oleate and ethyl oleate, remained intact for 72 months. We have also discovered that a formulation stabilized with tertiary-butylhydroquinone retained bioactivity for 231 days, while an unstabilized formulation lost almost all bioactivity after 123 days. We have further discovered that stabilized brood pheromone increases pollen foraging among worker honey bees, and stimulates pollen diet consumption. Lastly, we have discovered that a stabilized brood pheromone formulation using technical-grade components, with a composition that varies slightly from the natural composition achieved with reagent-grade components, has the same biological effect as a reagent-grade formulation. Such durability and robustness enables the development and sustained use of commercial products based on the brood pheromone stabilized with food-grade antioxidants.

This invention also pertains to compositions in which two or more of the ten pheromone components, comprised of methyl palmitate, ethyl palmitate, methyl stearate, ethyl stearate, methyl oleate, ethyl oleate, methyl linoleate, ethyl linoleate, methyl linolenate and ethyl linolenate, are formulated in effective amounts with food-grade antioxidants, including (but not limited to) butylated hydroxyanisole, butylated hydroxytolulene, tertiary-butyl hydroquinone, polypropylene glycol, citric acid and vitamin E and its derivatives. These compositions can be delivered to honey bees within a hive on an inert substrate, including (but not limited to) paraffin, vegetable wax, beeswax, silica, alumina, cellulose, modified cellulose (paper and paper products), dried plant tissue, wood or a synthetic polymer. These compositions can be used to manipulate the behavior of honey bee workers, including (but not limited to): increasing the ratio of pollen to non-pollen foragers, lowering the age of first foraging, inducing foraging behavior, stimulating pollen collection and transport of pollen back to the hive, stimulating consumption of supplementary diet components and antibiotics, inhibiting swarming and improving pollination of target crops. The stabilized pheromone compositions can also be used to stimulate the development and production of protein by the hypopharyngeal food gland. Combined application of stabilized brood pheromone compositions with the honey bee queen mandibular gland pheromone can be used to improve conditions within the hive and enhance the pollination of target crops.

EXAMPLE 1

Formulation

Because of the possibility of tainting honey, only food-grade antioxidants were considered as potential stabilizers. Brood pheromone was formulated with tertiary-butylhydroquinone as a test stabilizer in the following proportions (percentages weight/weight) and amounts as follows: methyl palmitate 3% (0.0225 g), ethyl palmitate 3% (0.0225 g), methyl stearate 17% (0.1275 g), methyl oleate 24.95% (0.1871 g), ethyl stearate 7% (0.0525 g), ethyl oleate 8% (0.0600 g), methyl lineoleate 2% (0.0150 g), ethyl linoleate 1% (0.0075 g), methyl linolenate 21% (0.1575 g), ethyl linolenate 13% (0.0975 g), and tertiary-butylhydroquinone 0.05% (0.0004 g). Components were mixed at approximately 20° C. in the above order using a magnetic stirrer and were blended until homogenous, resulting in 0.75 g of product.

EXAMPLE 2

Chemical Stability

Short-term and long-term stability studies were conducted, with simplified blends of potentially unstable brood pheromone components mixed in approximately the same proportions as in Example 1. Short-term evaluation for a two-week duration was done on blends of methyl oleate, methyl linoleate and methyl linolenate, and ethyl oleate, ethyl linoleate and ethyl linolenate, each with and without tertiary-butylhydroquinone. Twenty-week tests were done with identical blends as for the two-week experiments, but 72-week tests had methyl and ethyl palmitate and stearate added in the appropriate proportions to their respective blends. Approximately 250 mg of a blend was placed in a 4 mL (15×45 mm) plastic vial (Chromatographic Specialties) fitted with a diffusion insert screw cap (Agilent Technologies) with a 1 mm diameter hole to allow air circulation over the sample. All blends were continuously held at a constant temperature of 30° C.

For analysis by capillary gas chromatography, approximately 1 mg of a blend was dissolved in 1 mL of diethyl ether, and a 1 μL aliquot of each extract was analyzed. Analyses were done at time zero and after the given duration of exposure to air at 30° C., using a Hewlett Packard HP5890 gas chromatograph equipped with a flame ionization detector and a 30 m long BPX-70 capillary column (J&W Scientific). The injector and detector temperatures were 260° C. and 285° C., respectively. The temperature program was 80° C. rising at 5° C. per min for 24 min to 200° C., and then rising at 20° C. per min for 3 min to 260° C.

Figure 2:
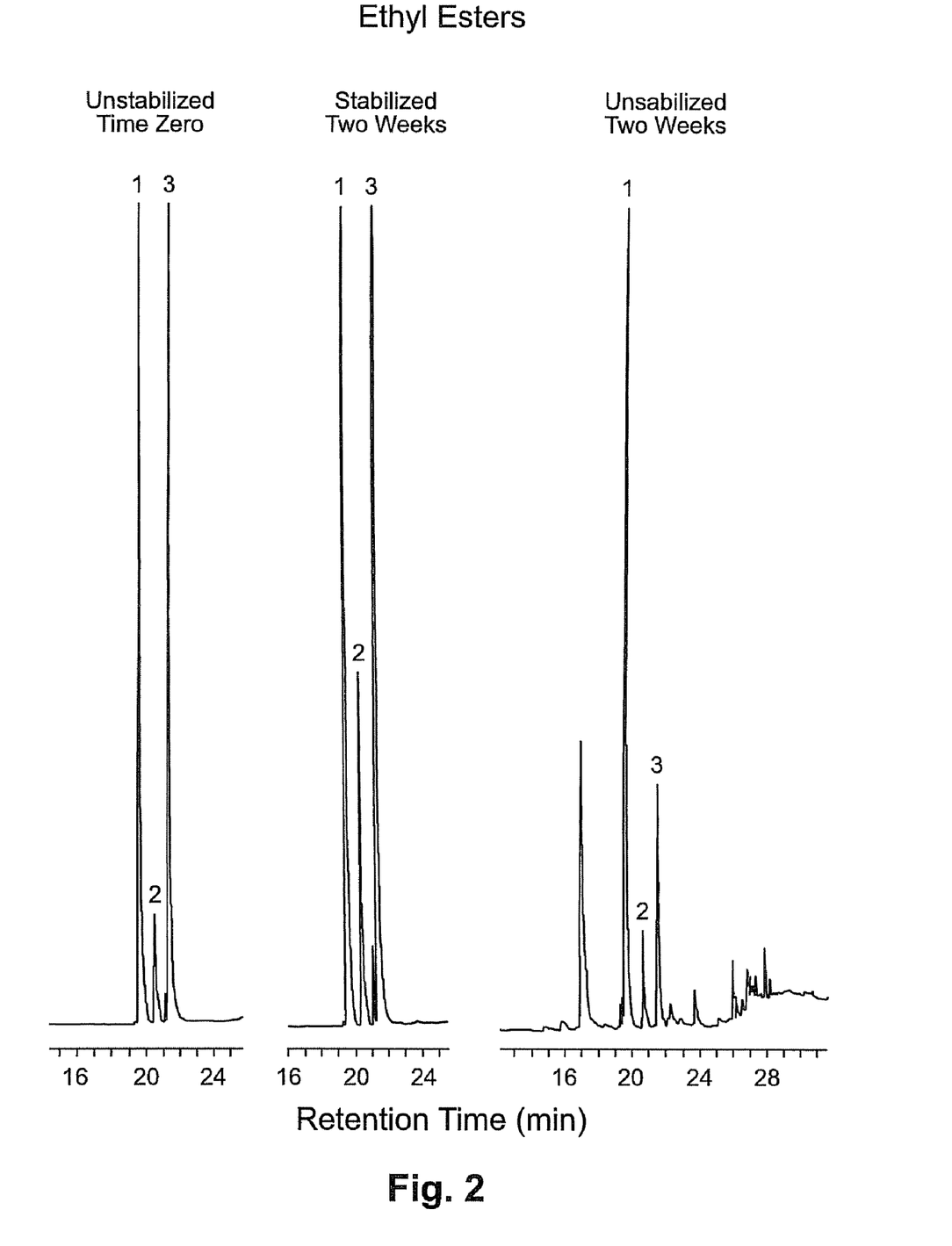
FIG. 2 illustrates gas chromatograph tracings of blends of ethyl oleate (1), ethyl linoleate (2) and ethyl linolenate (3) formulated with the antioxidant stabilizer tertiary-butylhydroquinone at time zero and at two weeks after exposure to air at room temperature (approximately 20° C.), in comparison to an otherwise identical unstabilized formulation after two weeks exposure at 20° C.
Figure 3:
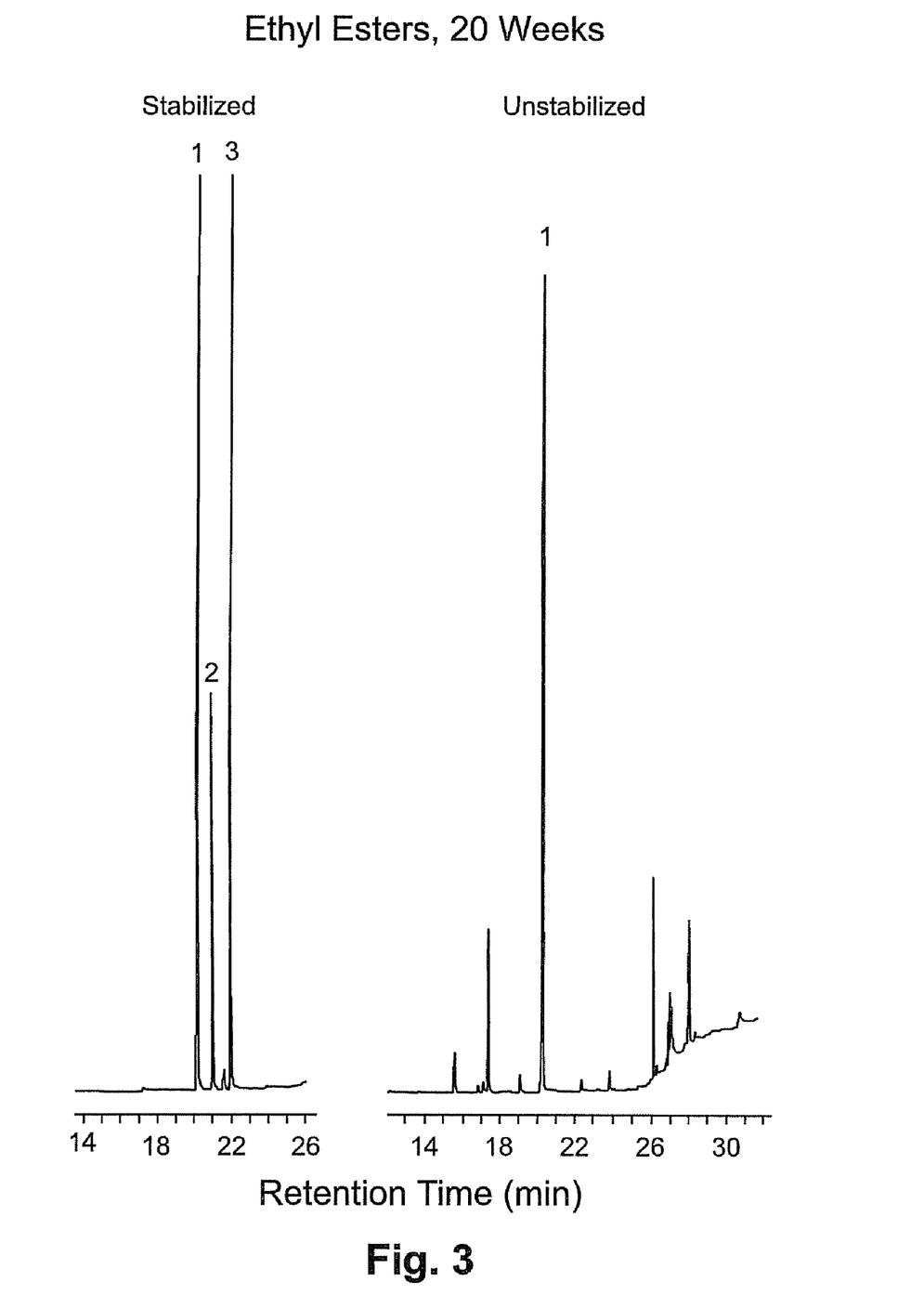
FIG. 3 illustrates gas chromatograph tracing of blend of ethyl oleate (1), ethyl linoleate (2) and ethyl linolenate (3) formulated with the antioxidant stabilizer tertiary-butylhydroquinone after 20 weeks exposure to air at room temperature (approximately 20° C.), in comparison to tracing of an otherwise identical unstabilized formulation after 20 weeks exposure at 20° C.
Figure 4:
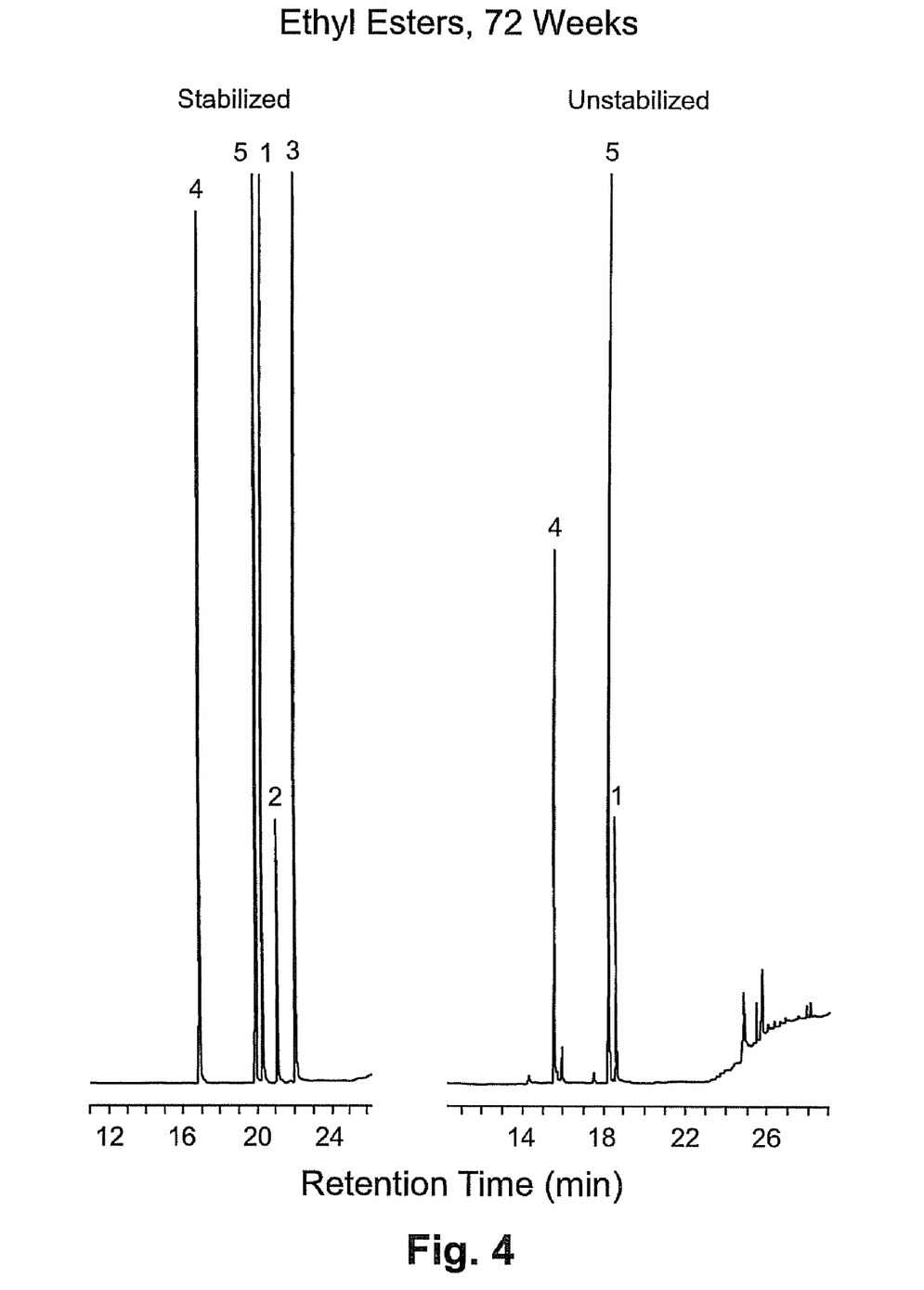
FIG. 4 illustrates gas chromatograph tracing of blend of ethyl oleate (1), ethyl linoleate (2), ethyl linolenate (3), ethyl palmitate (4) and ethyl stearate (5) formulated with the antioxidant stabilizer tertiary-butylhydroquinone after 72 weeks exposure to air at room temperature (approximately 20° C.), in comparison to tracing of an otherwise identical unstabilized formulation after 72 weeks exposure at 20° C.

Two-week results are given for methyl and ethyl esters (FIGS. 1 and 2), while long-term 20-week and 72-week results are given for only ethyl esters (FIGS. 3 and 4). Long-term results for methyl esters were virtually identical to those for the ethyl esters.

Figure 1:
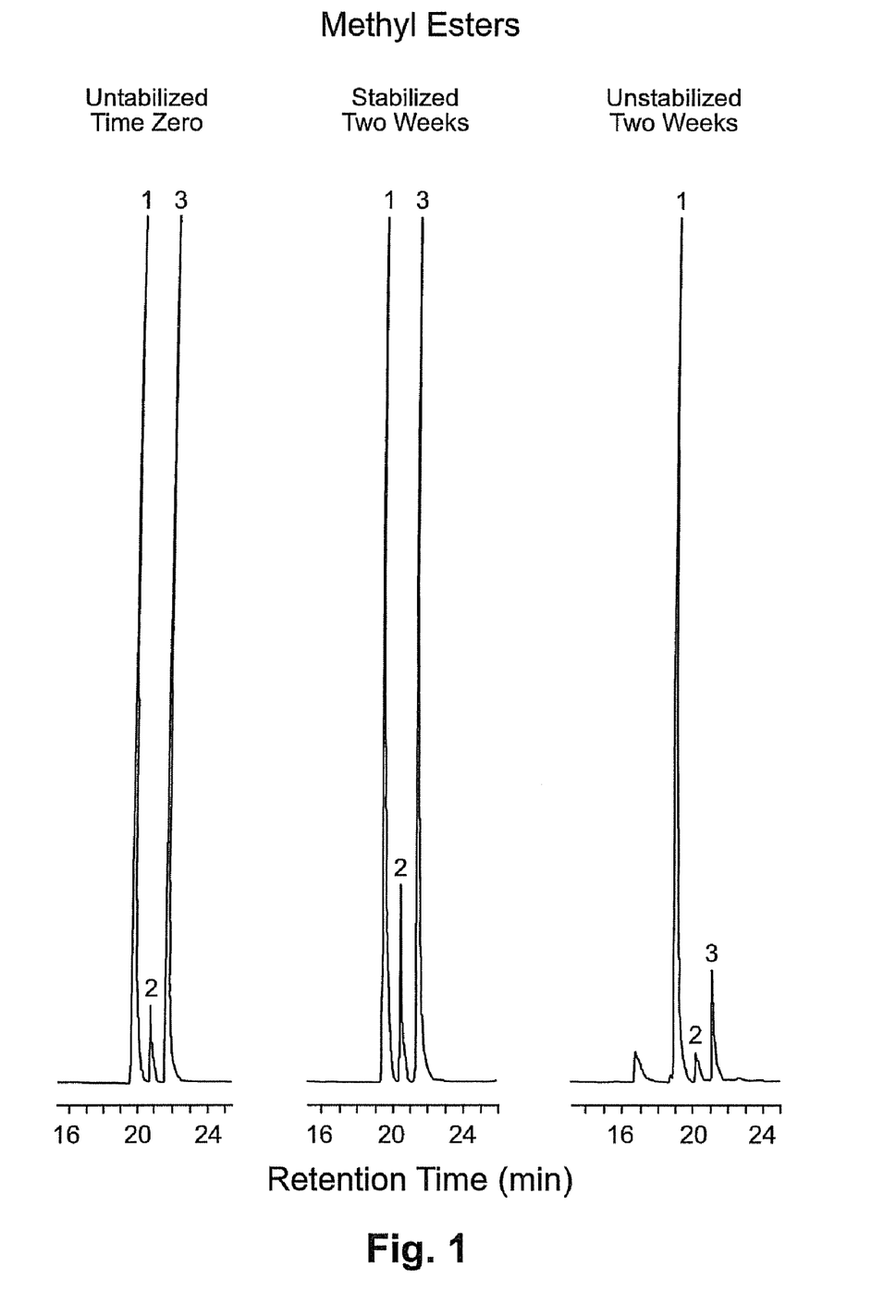
FIG. 1 illustrates gas chromatograph tracings of blends of methyl oleate (1), methyl linoleate (2) and methyl linolenate (3) formulated with the antioxidant stabilizer tertiary-butylhydroquinone at time zero and at two weeks after exposure to air at room temperature (approximately 20° C.), in comparison to an otherwise identical unstabilized formulation after two weeks exposure at 20° C.

After two weeks, the proportional composition of methyl esters in the blend that was stabilized with tertiary-butylhydroquinone remained the same as in the unstabilized blend at time zero (FIG. 1). However, in the unstabilized blend, after two weeks, the amount of methyl linoleate had fallen by 85%, and the amount of methyl linolenate had decreased by 90%. Because of breakdown of the other components, the proportional composition of methyl oleate had risen from 48% of the total blend to 82%. Similar results were obtained with the ethyl esters after two weeks. The amount of ethyl linoleate fell by 74%, and the amount of ethyl linolenate decreased by 94%, while ethyl oleate rose from 40% of the total blend to 66% (FIG. 2). These results indicate that breakdown of methyl and ethyl linoleate and linolenate occurs rapidly at room temperature, and would probably result in complete loss of bioactivity of the full pheromone blend after 2-4 weeks. The results also indicate that without stabilization, the shelf life of any brood pheromone product would be unacceptably short.

After 20 and 72 weeks at 20° C., the proportional composition of ethyl oleate, ethyl linoleate and ethyl linolenate in the stabilized blends (FIGS. 3 and 4, respectively) remained essentially the same as in the stabilized blend after two weeks exposure (FIG. 2). In contrast, after 20 weeks, no ethyl linoleate and no ethyl linolenate remained in the unstabilized blend, and the amount of ethyl oleate had risen only slightly from 37% to 43% of the total blend, despite the complete absence of the other two major components (FIG. 3). This indicates complete breakdown of ethyl linoleate and ethyl linolenate after 20 weeks exposure, and also suggests partial breakdown of ethyl oleate.

As expected from the results in FIG. 3, no ethyl linoleate or ethyl linolenate remained after 72 weeks of exposure to room temperature, indicating complete breakdown of these two pheromone components (FIG. 4). The percentage compositions of ethyl palmitate and ethyl stearate rose from 8% and 23% to 20% and 57%, respectively, suggesting no breakdown even after 72 weeks. However, the percentage of ethyl oleate fell from 24% to 10%. Together with the results after 20 weeks, this decline confirms a slow breakdown of ethyl oleate in the unstabilized formulations.

These results indicate that stabilization of honey bee brood pheromone with tertiary-butylhydroquinone will result in no breakdown of any unstable pheromone component for well over a year. The lack of even a slight indication of breakdown after 72 weeks (FIG. 4) suggests that the shelf life of a stabilized pheromone formulation will be at least two years. This is a sufficiently long duration to justify development of a commercial product.

EXAMPLE 3

Longevity of Stabilized Brood Pheromone Measured by Sucrose Response Threshold Honey bees respond reflexively by extending the proboscis when a drop of sucrose solution is applied to the antennae. This is called the proboscis extension response threshold (PER-RT) assay to sucrose. The assay consists of a sucrose concentration course of 0.1, 0.3, 1, 3, 10 and 30% (wt/vol), corresponding to a logarithmic series of −1, −0.5, 0, 0.5, 1 and 1.5. The antenna of each bee is touched once with a droplet of sucrose. The lowest concentration that causes proboscis extension is interpreted as an estimate of individual sucrose response threshold (Page et al. 1998; Pankiw and Page 1999). The results from the PER assay with ascending concentrations of sucrose are transformed to sucrose scores. A PER score is directly related to the response threshold of the individual bee, because most bees continue to respond to all increasing concentrations of sucrose following initial response. A PER score of 6, wherein an individual bee responds to all 6 sucrose concentrations, beginning with 0.1% sucrose in the PER assay, represents a response threshold 300 times lower than a score of 1, wherein an individual responds only to 30% sucrose. The response threshold (RT) of an individual bee is a "window" into the neurosensory system that is correlated with foraging behavior (Pankiw and Page 2000), and age (Pankiw and Page 1999; Pankiw 2003), and is modulated by brood pheromone (Pankiw and Page 2001, 2003). We used the PER-RT assay to sucrose as one method of assessing the bioactivity of stabilized brood pheromone stored for various durations at room temperature.

Honey bees from at least six unrelated "wild-type" sources were emerged for 3 h from their combs in an incubator maintained at 33° C. and 55% RH. Three hundred newly-emerged bees were randomly placed into plexiglass wire mesh cages (14.6×10×7.7 cm). Cages were provided with 30% sucrose solution, water ad libitum, and reared in the above incubator conditions. Individual cages were randomly selected for the following treatments: 1) unstabilized brood pheromone stored at room temperature, 2) brood pheromone stabilized with tertiary-butyl hydroquinone and stored at room temperature, 3) freshly prepared unstabilized brood pheromone, and 4) a control with no pheromone. The composition of the prepared pheromone was: ethyl linoleate 1%, ethyl linolenate 13%, ethyl oleate 8%, ethyl palmitate 3%, ethyl stearate 7%, methyl linoleate, 2%, methyl linolenate 21%, methyl oleate 25%, methyl palmitate 3% and methyl stearate 17%. Pheromone-treated cages received 300 larval equivalents (LEq) per day (1:1 ratio of brood pheromone to bees). The pheromone was formulated in isopropanol such that 300 LEq was delivered in approximately 15 μL of solution. The control cages received an equal volume of isopropanol daily. Respective treatments were delivered daily on a glass plate (7×8 cm) after the isopropanol was evaporated. Bees were reared as above for six days, and then tested for their sucrose response threshold as described above. This protocol was followed on days 48, 123 and 231 after the preparation of unstabilized and stabilized formulations of brood pheromone. Between treatment, scores were compared using Kruskal-Wallis and Mann-Whitney U tests.

Stabilized brood pheromone showed bioactivity that was no different from freshly formulated brood pheromone (Table 1). Honey bees exposed to stabilized brood pheromone consistently showed a sucrose response threshold that was at least 1.75 times higher than the response of unexposed bees in control cages. Additionally, sucrose responsiveness of honey bees exposed to unstabilized brood pheromone stored at room temperature for 48, 123 and 231 days was not significantly different from that of control bees exposed to no pheromone.

These results demonstrate that stabilized brood pheromone shows long-term bioactivity when stored at room temperature. This bioactivity is statistically the same as that induced by freshly-formulated brood pheromone. The results also indicate that addition of tertiary-butylhydroquinone to the ten pheromone components had no effect on bioactivity of the pheromone.

TABLE 1

Bioactivity of unstable and stabilized brood pheromone stored at room temperature versus freshly formulated brood pheromone as a percent of sucrose responsiveness in honey bees held in a no-pheromone control environment. Probabilities below each value indicate likelihood that sucrose responsiveness was similar to that of bees in the no-pheromone control environment.

| Days at room temperature | Unstable brood pheromone % | Stabilized brood pheromone % | Freshly-formulated unstable brood Pheromone |
|---|---|---|---|
| 48 | 17.0 (P > 0.05) | 88.1 (P < 0.01) | 78.7 (P < 0.001) |
| 123 | 6.8 (P > 0.05) | 75.6 (P < 0.001) | 68.5 (P < 0.001) |
| 231 | 3.7 (P > 0.05) | 89.7 (P < 0.0001) | 91.0 (P < 0.0001) |

EXAMPLE 4

Brood Pheromone Formulated from Reagent-Grade and Technical-Grade Fatty Acid Esters Releases Honey Bee Pollen Foraging All previous formulations of brood pheromone were comprised of reagent grade compounds of greater than 99% purity supplied by Sigma-Aldrich (St. Louis, Mo.). Reagent grade compounds are most commonly used as standards in chemical identification, for chemical synthesis, or in any other application where purity is essential. However, amount of purity is directly proportional to the cost of a compound. One way to reduce the cost of brood pheromone is to formulate it using less pure, technical grade components. Although cost is significantly reduced with technical grade components there is a trade-off. Technical grade components are derived from natural sources containing blends of fatty acids not in the exact proportions of the natural brood pheromone. We hypothesized that bees exposed to brood pheromone formulated from either reagent-grade or technical-grade components would forage for pollen at a higher level than bees exposed to no pheromone.

This experiment was replicated six times on Jun. 7, 2005. Typical honey bee colonies were randomly selected to receive one of the following treatments; 1) control, blank glass plate, 2) reagent-grade brood pheromone stabilized with tertiary-butyl hydroquinone, or 3) similarly stabilized technical-grade brood pheromone. Pheromone blends were formulated with tertiary-butyl hydroquinone according to the proportions given in Table 2. A total of 1.12 mg of total esters was applied to a glass plate (20 cm×10 cm), and the plate was placed in the center of the brood nest area of the colony. One hour later, we conducted five minute entrance counts of returning pollen and non-pollen foragers. Pollen foragers are visibly apparent because pollen is carried outside the body on specialized areas of the hind legs called the corbiculae. Liquid loads such as nectar and water are carried internally in the crop and are not visibly apparent. When type, presence or absence of load is not visibly apparent, such returning bees are classified as non-pollen foragers. Observers use hand-held tally counters, one hand for pollen and one hand for non-pollen foragers. Each colony was measured two times per hour for two hours by two different people for a total of four five-minute counts per colony. The people performing the counts were blind to the treatments.

Count data were analyzed using Contingency Table Analysis. Compared to the no pheromone blank control, both the technical-grade ($\chi^2=7.0$, df=1, P<0.01) and the reagent-grade ($\chi^2=15.0$, df=1, P<0.0001) formulations induced significantly greater ratios of pollen to non-pollen foragers entering colonies (Table 3). The reagent-grade formulation released a slightly higher proportion of pollen foragers than the technical grade formulation ($\chi^2=3.9$, df=1, P=0.048).

Two pertinent findings arise from this study. First, stabilized brood pheromone of either grade is capable of inducing enhanced pollen foraging. Second, technical-grade formulated brood pheromone increased the proportion of pollen foragers by approximately 116% over the no pheromone control treatment, only 3.5% less than that induced by the reagent-grade formulation. Thus, at a cost of only 7% of the reagent-grade formulation, technical-grade formulated brood pheromone stabilized with tertiary-butyl hydroquinone appears to be an efficacious and economically viable product.

TABLE 2

Formulation of reagent-grade and technical-grade brood pheromone.

| Compound | Reagent-grade fatty acid esters + 0.05% tertiary-butyl hydroquinone (% of total esters) | Technical-grade fatty acid esters + 0.05% tertiary-butyl hydroquinone (% of total esters) |
|---|---|---|
| Methyl Palmitate | 3.00 | 2.03 |
| Ethyl Palmitate | 3.00 | 4.23 |
| Methyl Stearate | 17.00 | 15.17 |
| Methyl Oleate | 25.00 | 25.04 |
| Ethyl Stearate | 7.00 | 8.88 |
| Ethyl Oleate | 8.00 | 6.72 |
| Methyl Linoleate | 2.00 | 8.63 |
| Ethyl Linoleate | 1.00 | 3.5 |

TABLE 2-continued

Formulation of reagent-grade and technical-grade brood pheromone.

| Compound | Reagent-grade fatty acid esters + 0.05% tertiary-butyl hydroquinone (% of total esters) | Technical-grade fatty acid esters + 0.05% tertiary-butyl hydroquinone (% of total esters) |
|---|---|---|
| Methyl Linolenate | 21.00 | 17.07 |
| Ethyl Linolenate | 13.00 | 8.73 |

TABLE 3

Ratio of pollen to non-pollen foragers entering colonies in a 5 min period.

| Treatment | Ratio of pollen/non-pollen foragers | Probability[1] |
|---|---|---|
| Control | 0.38 | |
| Technical-grade fatty acid esters + Tertiary-butyl hydroquinone) | 0.82 | <0.01 |
| Reagent-grade fatty acid esters + Tertiary-butyl hydroquinone) | 0.85 | <0.0001 |

[1]Contingency Table Analysis probabilities where the null hypothesis is that control and treatment ratios are the equal.

EXAMPLE 5

Stimulation of Pollen Diet Consumption

This experiment was conducted from 1-15 Mar. 2004. Twelve typical colonies from Texas A&M University apiaries were randomly selected. Colony measures were estimated by the use a grid divided into square sections, 6.45 cm$^2$. The area covered by bees was converted to bee numbers; approximately 1.5 bees per cm$^2$ (Pankiw and Page 2001; Pankiw et al. 2002). Comb area occupied by eggs, larvae, and pupae collectively known as brood were measured. Six colonies were randomly selected to receive daily treatment of brood pheromone at three larval equivalents/bee/day (1.55 µg/bee/day), and six colonies received a blank glass plate. A dose of three larval equivalents/bee/day is known to increase amount of pollen foraging in large colonies (Pankiw and Page 2001). Each colony was provisioned with a commercially available pollen diet supplement: 450 g of Brood Builder™ (Dadant & Sons, Hamilton, Ill.) shaped like a hamburger patty between two pieces of scored wax paper. Fresh patties were provided upon consumption of the previous patty. Every three days for fifteen days colonies were inspected for patty consumption. A new patty was provided to colonies that fully consumed the previous patty. Colony measures were conducted on days 7 and 15. All colonies received a fresh pollen supplement patty regardless of amount used on day 7. Unconsumed old patties were removed and weighed to estimate amount consumed.

Analysis of variance was used to compare pheromone treated and control colonies. It was not necessary to perform analysis of co-variance because at the outset of the experiment number of bees and amounts of comb space used by brood, pollen, honey, and empty cells was not significantly different (P>0.05) between treatment groups.

Colonies treated with brood pheromone consumed significantly more pollen supplement than did control colonies in weeks 1 and 2 (Table 4). Brood area was not different between treatments in week 1 ($F_{1,11}$=0.3, P>0.05). In week 2 brood area was significantly greater in the brood pheromone treated group ($F_{1,11}$=10.6, P<0.01; Table 2).

These results indicate that stabilized brood pheromone can be used to stimulate consumption of food, resulting in increased production of brood, which in turn can lead to greater colony vigor. Increased consumption of food can also be exploited by incorporating dietary supplements or antibiotics into a pollen patty or other food source.

TABLE 4

Comparison of pollen consumption and brood area between honey bee colonies exposed to brood pheromone and unexposed control colonies.

| Treatment/ statistics | Consumption (g) | | Brood area (cm$^2$)* | |
|---|---|---|---|---|
| | wk 1 | wk 2 | wk 1 | wk 2 |
| Brood pheromone | 406.6 ± 9.5 | 422.5 ± 17.0 | 3928 ± 586 | 2975 ± 330 |
| Control | 185.0 ± 21.4 | 178.3 ± 27.2 | 3472 ± 668 | 1800 ± 142 |
| ANOVA $F_{1,11}$ | 89.7 | 57.2 | 0.3 | 10.7 |
| Probability | .0001 | .0001 | 0.6 | 0.008 |

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

REFERENCES

US Patent Documents

Page, R. E. Jr. and T. Pankiw. 2002. Synthetic bee pollen foraging pheromone and uses thereof. U.S. Pat. No. 2002/0182977 A1.

Other Publications

Anderson, C. A. and N. R. Franks, 2001. Teams in animal societies. Behav. Ecol. 12:534-540.

Al-Tikrity, W. S., A. W. Benton, R. C. Hillman and W. W. Clarke, Jr. 1972. The relationship between the amount of unsealed brood in honeybee colonies and their pollen collection. J. Apic. Res. 11: 9-12.

Barker, R. J. 1971. The influence of food inside the hive on pollen collection. J. Apic. Res. 10: 23-26.

Crailsheim, K., L. H. W. Schneider, N. Hrassnigg, G. Bühlmann, U. Brosch, R. Gmeinbauer, and B. Schöffmann. 1992. Pollen consumption and utilization in worker honeybees (Apis mellifera carnica): dependence on individual age and function. J. Insect Physiol. 38: 409-419.

Filmer, R. S. 1932. Brood area and colony size as factors in activity of pollination units. J. Econ. Entomol. 25: 336-343.

Free, J. B. 1967. Factors determining the collection of pollen by honeybee foragers. Anim. Behav. 15: 134-144.

Free, J. B. 1979. Managing honeybee colonies to enhance the pollen-gathering stimulus from brood pheromones. Appl. Anim. Ethol. 5: 173-178.

Herbert, E. W. 1992. Honey bee nutrition. Pp. 197-233. In: Graham, J. M. (ed.). The hive and the honey bee. Rev. Ed. Dadant & Sons, Hamilton, Ill.

Jaycox, E. R. 1970. Honey bee queen pheromones and worker foraging behavior. Ann. Entomol. Soc. Am. 63: 222-228.

LeConte, Y., G. Arnold, J. Trouiller and C. Masson. 1990. Identification of a brood pheromone in honeybees. Nattirwissenschaften 81: 462-465.

LeConte, Y., A. Mohammedi and G. E. Robinson. 2000. Primer effects of a brood pheromone on honeybee behavioural development. Proc. R. Soc. London B 268: 163-168.

Lindauer, M. 1952. Ein Beitrag zur Frage der Arbeitsteilung im Bienenstaat. Z. Vergl. Physiol. 34: 299-345.

Page, R. E., Jr., J. Erber and M. K. Fondrk. 1998. The effect of genotype on response thresholds to sucrose and foraging behavior of honey bees (*Apis mellifera* L.). J. Comp. Physiol. A 182: 489-500.

Pankiw, T. 2003. Directional change in a suite of foraging behaviors in tropical and temperate evolved honey bees (*Apis mellifera* L.). Behav. Ecol. Sociobiol. 54: 458-464.

Pankiw, T. 2004a. Cued in: honey bee pheromones as information flow and collective decision making. Apidologie 35: 217-226.

Pankiw, T. 2004b. Brood pheromone regulates foraging activity of honey bees (*Hymenoptera*: Apidae). J. Econ. Entomol. 97: 748-751.

Pankiw, T. and R. E. Page, Jr. 1999. The effects of genotype, age, sex, and caste on response thresholds to sucrose and foraging behavior of honey bees (*Apis mellifera* L.). J. Comp. Physiol. A 185: 207-213.

Pankiw, T. and R. E. Page, Jr. 2000. Response thresholds to sucrose predict foraging division of labor in honey bees. Behav. Ecol. Sociobiol. 47: 265-267.

Pankiw, T. and R. E. Page, Jr. 2001. Brood pheromone modulates sucrose response threshold in honeybees (*Apis mellifera* L.). Behav. Ecol. Sociobiol. 49: 206-213.

Pankiw, T. and R. E. Page, Jr. 2003. Effect of pheromones, hormones and handling on sucrose response thresholds of honey bees (*Apis mellifera* L.). J. Comp. Physiol. A 188: 675-684.

Pankiw, T. and W. L. Rubink. 2002. Pollen foraging response to brood pheromone by Africanized and European honey bees (*Apis mellifera*). Ann. Entomol. Soc. Am. 95: 761-767.

Pankiw, T., R. E. Page, Jr. and M. K. Fondrk. 1998. Brood pheromone stimulates pollen foraging in honey bees (*Apis mellifera*). Behav. Ecol. Sociobiol. 44: 193-198.

Pankiw, T., C. M. Nelson, R. E. Page, Jr. and M. K. Fondrk. 2004a. The communal crop: Modulation of sucrose response thresholds of pre-foraging honey bees with incoming nectar quality. Behav. Ecol. Sociobiol. 55: 286-292.

Pankiw, T., R. Roman, R. R. Sagili and K. Zhu-Salzman. 2004b. Pheromone-modulated behavioral suites influence colony growth in the honey bee (*Apis mellifera*). Naturwissenschaften 91: 575-578.

Robinson, G. E. 1992. Regulation of division of labor in insect societies. Ann. Rev. Entomol. 37: 637-665.

Seely, T. D. and S. A. Kolmes. 1991. Age polytheism for hive duties in honey bees—illusion or reality. Ethology 87: 284-297.

Todd, F. E. and C. B. Reed. 1970. Brood measurement as a valid index to the value of honey bees as pollinators. J. Econ. Entomol. 63: 148-149.

What is claimed is:

1. A method of stabilizing a honey bee brood pheromone comprised of ten compounds, namely ethyl linoleate, ethyl linolenate, ethyl oleate, ethyl palmitate, ethyl stearate, methyl linoleate, methyl linolenate, methyl oleate, methyl palmitate and methyl stearate, which comprises incorporating with the ten compounds an effective amount of tertiary-butyl hydroquinone wherein the weight proportions of the compounds are methyl palmitate (3%), ethyl palmitate (3%), methyl stearate (17%), methyl oleate (24.95%), ethyl stearate (7%), ethyl oleate (8%), methyl linoleate (2%), ethyl linoleate (1%), methyl linolenate (0.05%), ethyl linolenate (0.05%) and tertiary-butyl hydroquinone (0.05%).

* * * * *